US008000778B2

(12) United States Patent
Seim et al.

(10) Patent No.: US 8,000,778 B2
(45) Date of Patent: Aug. 16, 2011

(54) ATRIAL TACHYARRHYTHMIA DETECTION SYSTEM AND METHOD

(75) Inventors: Gary Seim, Minneapolis, MN (US); David Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1932 days.

(21) Appl. No.: 10/980,009

(22) Filed: Nov. 3, 2004

(65) Prior Publication Data

US 2005/0065564 A1 Mar. 24, 2005

Related U.S. Application Data

(62) Division of application No. 09/827,763, filed on Apr. 6, 2001, now Pat. No. 6,895,272.

(51) Int. Cl.
*A61B 5/0452* (2006.01)
(52) U.S. Cl. ......... 600/509; 600/510; 600/513; 600/518
(58) Field of Classification Search ............... 607/6, 14, 607/17, 25; 600/509, 510, 513, 518
See application file for complete search history.

(56) References Cited

U.S. PATENT DOCUMENTS

| 4,253,466 A | | 3/1981 | Hartlaub et al. |
| 5,074,308 A | * | 12/1991 | Sholder et al. ............... 600/510 |
| 5,269,299 A | * | 12/1993 | Duncan ........................... 607/9 |
| 5,840,079 A | | 11/1998 | Warman et al. |
| 5,978,707 A | | 11/1999 | Krig et al. |
| 6,493,579 B1 | | 12/2002 | Gilkerson et al. |
| 6,658,286 B2 | | 12/2003 | Seim |
| 6,711,438 B1 | * | 3/2004 | McClure et al. ................ 607/9 |

* cited by examiner

*Primary Examiner* — Carl H Layno
*Assistant Examiner* — Natasha N Patel
(74) *Attorney, Agent, or Firm* — Hollingsworth & Funk, LLC

(57) ABSTRACT

A system and method provide for detecting atrial arrhythmias within an implantable medical device capable of sensing and pacing at least an atrium of a heart. Arrhythmia of the atrium is detected. In response to detecting atrial arrhythmia, delivery of pacing signals to the atrium is inhibited under certain conditions. While delivery of the pacing signals to the atrium is inhibited, the detected arrhythmia of the atrium is confirmed during a period of further evaluation. Delivery of pacing signals to the atrium is enabled upon ceasing of the atrial arrhythmia. Inhibiting delivery of the pacing signals during atrial arrhythmia evaluation advantageously provides for an increase in the rate at which the detected arrhythmia is confirmed.

25 Claims, 7 Drawing Sheets

ATRIAL TACHYARRHYTHMIA DETECTION SYSTEM AND METHOD

RELATED PATENT DOCUMENTS

This is a divisional of U.S. patent application Ser. No. 09/827,763, filed on Apr. 6, 2001, now U.S. Pat. No. 6,895,272, to which Applicant claims priority under 35 U.S.C. §120, and which is incorporated herein by reference.

FIELD OF THE INVENTION

The present invention relates generally to implantable medical devices and, more particularly, to implantable pacemakers and cardioverter-defibrillators that detect and treat atrial tachyarrhythmias.

BACKGROUND OF THE INVENTION

Implantable cardioverter-defibrillators (ICDs) have been developed that employ detection algorithms capable of recognizing and treating atrial tachycardias and atrial fibrillation. In general, ICDs are designed to treat such tachycardias with antitachycardia pacing and low-energy cardioversion shocks in conjunction with back-up defibrillation therapy. These ICDs monitor the heart rate and the onset of the arrhythmia by sensing endocardial signals and determining when the heart is in need of either cardioversion to treat a given tachycardia or of defibrillation to treat a fibrillation condition.

While the combination of antitachycardia pacing with low and high energy shock delivery, as well as backup bradycardia pacing, in ICDs has expanded the number of clinical situations in which the devices may appropriately be employed, improved means of coordinating atrial rate information in a way that results in a system that effectively and efficiently treats atrial tachyarrhythmias is still desired.

For the reasons stated above, and for other reasons stated below which will become apparent to those skilled in the art upon reading the present specification, there is a need in the art for improved atrial arrhythmia detection techniques. There exists a further need for such techniques that provide for an increase in the speed at which atrial arrhythmias are evaluated and confirmed. The present invention fulfills these and other needs.

SUMMARY OF THE INVENTION

The present invention is directed to a system and method for detecting atrial arrhythmias. An atrial arrhythmia detection methodology of the present invention is implemented with an implantable medical device capable of sensing and pacing at least an atrium of the heart. According to one embodiment, arrhythmia of the atrium is detected. In response to detecting arrhythmia of the atrium, delivery of pacing signals to the atrium is inhibited to prevent competitive pacing of the atrium. While delivery of the pacing signals to the atrium is inhibited, the detected arrhythmia of the atrium is confirmed during a period of further evaluation. Inhibiting delivery of the pacing signals during atrial arrhythmia evaluation advantageously provides for an increase in the rate at which the detected arrhythmia is confirmed. Delivery of pacing signals to the atrium is enabled after the detected atrial arrhythmia has ceased.

According to an embodiment of the present invention, high atrial interval rates indicative of atrial arrhythmia are detected. Delivery of pacing signals to the atrium is inhibited in response to detecting the high atrial interval rates, such as in response to detecting atrial flutter or other atrial arrhythmias. For example, delivery of pacing signals to the atrium is inhibited in response to detecting atrial interval rates of between about 130 and 230 beats per minute (bpm). The detection threshold for inhibiting atrial pacing is programmable, typically between 130 and 230 bpm, with 170 bpm representing a nominal threshold.

Atrial intervals are detected while delivery of the pacing signals to the atrium is inhibited. Atrial intervals are classified in an atrial window. The atrial window has a length and an associated first satisfaction criterion. An atrial episode is declared in response to satisfying the atrial window by comparing classified atrial intervals to the first satisfaction criterion. Inhibiting delivery of the pacing signals during detection of high atrial interval rates advantageously provides for an increase in a rate of atrial window satisfaction.

In one approach, delivery of atrial paces is inhibited during a detection window initiated in response to detecting high atrial interval rates indicative of atrial arrhythmia. By way of example, an atrial event occurring within a post-ventricular atrial refractory period (PVARP) is detected. A detection window is initiated in response to the detected atrial event. Delivery of an atrial pace signal is inhibited during the duration of the detection window. A subsequent atrial event may be detected before expiration of the detection window. In this case, a subsequent detection window is initiated in response to the detected subsequent atrial event. Delivery of a subsequent atrial pace signal is inhibited during the subsequent detection window.

The atrial window may have a length that ranges between 20 and 60 atrial interval samples. The first satisfaction criterion represents a predetermined number, percentage or ratio of the atrial intervals classified as fast atrial intervals relative to the atrial window length. For example, the first satisfaction criterion may represent about 80 percent of the atrial intervals classified as fast atrial intervals.

Further processes may involve verifying that the declared atrial episode is a sustained atrial episode in response to the atrial window being satisfied by a second satisfaction criterion for subsequent atrial intervals. Each of the first and second satisfaction criterion represents a predetermined number, percentage or ratio of the atrial intervals classified as fast atrial intervals relative to the atrial window length, and the second satisfaction criterion is less than the first satisfaction criterion. By way of example, the first satisfaction criterion may represent about 80 percent of the atrial intervals classified as fast atrial intervals and the second satisfaction criterion may represent about 60 percent of the subsequent atrial intervals classified as fast atrial intervals.

In accordance with another embodiment of the present invention, atrial events occurring within a post-ventricular atrial refractory period (PVARP) are detected. One or more detection windows are initiated in response to the detected atrial events. Delivery of atrial pace signals is inhibited during the duration of the respective detection windows. While inhibiting delivery of the atrial pace signals, atrial intervals are classified in an atrial window having a length and an associated satisfaction criterion. An atrial episode is declared in response to satisfying the atrial window by comparing classified atrial intervals to the satisfaction criterion.

According to a further embodiment of the present invention, a body implantable system includes at least one lead comprising an atrial electrode for sensing and pacing an atrium of a heart. A detector, coupled to the lead, detects high atrial interval rates indicative of atrial arrhythmia. Memory is configured to define an atrial window having a first length and a first satisfaction criterion. A control circuit is coupled to the detector and memory. The control circuit inhibits delivery of pacing signals to the atrium in response to detecting the high atrial interval rates. The detector detects atrial intervals while inhibiting delivery of the pacing signals to the atrium. The control circuit classifies the atrial intervals in an atrial window and declares an atrial episode in response to satisfying the atrial window by comparing classified atrial intervals to the first satisfaction criterion.

The control circuit inhibits delivery of the pacing signals during a detection window initiated in response to detecting high atrial interval rates indicative of atrial arrhythmia. For example, the detector detects an atrial event occurring within a post-ventricular atrial refractory period (PVARP), and the control circuit initiates a detection window in response to the sensed atrial event and inhibits delivery of an atrial pace signal during the detection window. The detector further detects a subsequent atrial event occurring before expiration of the detection window. In this case, the control circuit initiates a subsequent detection window in response to the sensed subsequent atrial event and inhibits delivery of a subsequent atrial pace signal during the subsequent detection window.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
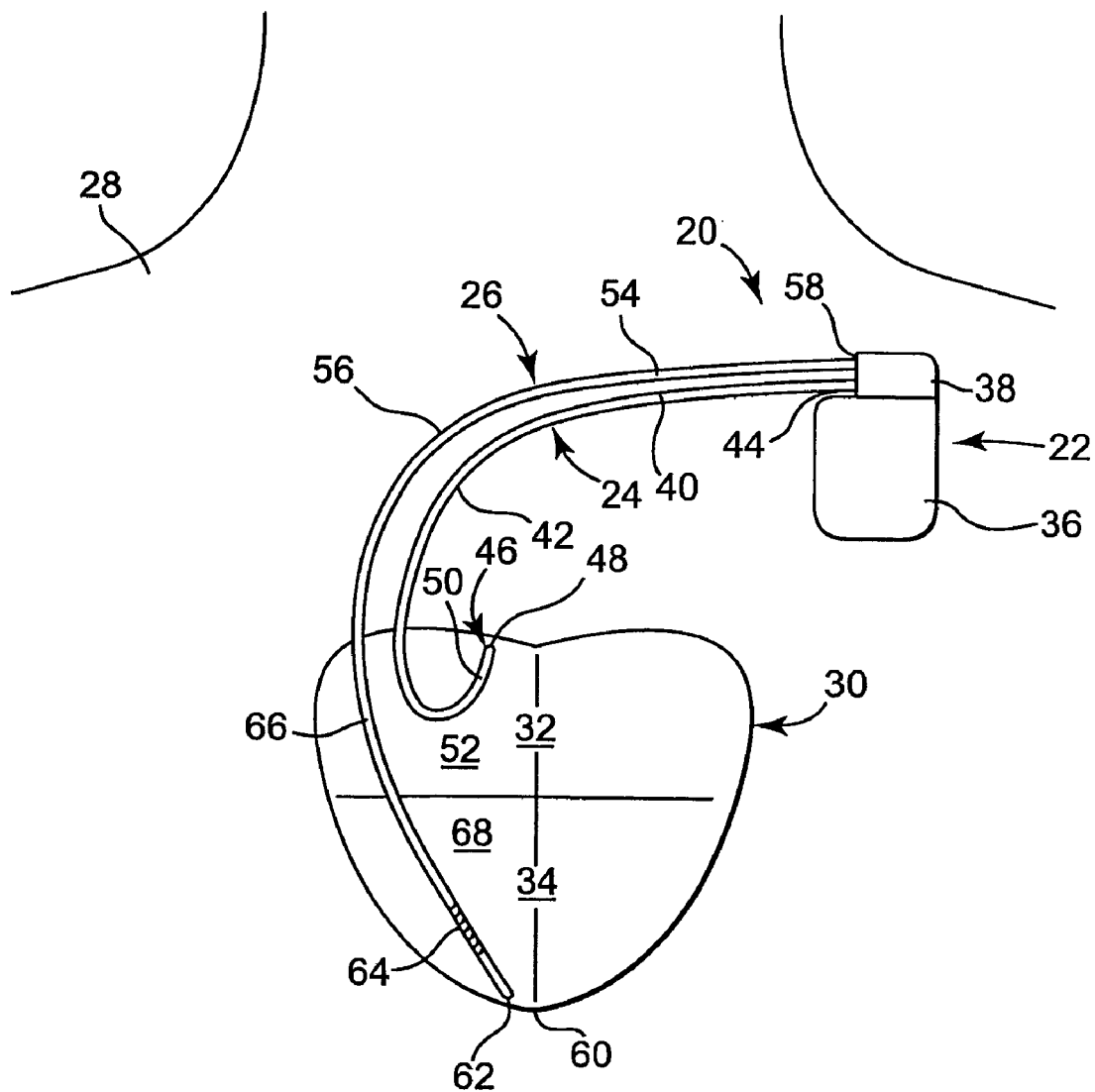
FIG. 1 is a depiction of an implantable medical device with which atrial arrhythmia detection methodologies of the present invention may be practiced.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown byway of illustration, various embodiments in which the invention may be practiced. It is to be understood that other embodiments may be utilized, and structural and functional changes may be made without departing from the scope of the present invention.

Referring now to the figures, and more particularly to FIG. 1, there is shown a body implantable system 20 that represents one of several types of systems with which atrial arrhythmia detection methodologies of the present invention may be practiced. For example, the implantable pulse generator 22 may be representative of all or part of a pacemaker, defibrillator, cardioverter, cardiac monitor, or re-synchronization device. Accordingly, the arrhythmia detection methodologies of the present invention may be practiced in a wide variety of implantable medical devices that sense cardiac activity.

The body implantable system 20 is shown to include an implantable pulse generator 22 coupled to an atrial lead 24 and a ventricular lead 26. The system 20 may also include endocardial pacing and cardioversion/defibrillation leads (not shown) that are advanced into the coronary sinus and coronary veins to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at a desired site.

It is understood that an atrial arrhythmia detection methodology of the present invention may be practiced without inclusion of the ventricular lead 26 and/or a coronary sinus lead, and in configurations in which only the atria are paced and sensed. It is further understood that an atrial arrhythmia detection approach consistent with the principles of the present invention may also be practiced in devices that provide for dual chamber pacing and sensing, such as that depicted in FIG. 1 and described in greater detail hereinbelow.

The system 20, as shown in FIG. 1, is implanted in a human body 28 with portions of the atrial and ventricular leads 24 and 26 inserted into a heart 30 to detect and analyze electric cardiac signals produced by both the atria 32 and the ventricles 34 of the heart 30. The atrial and ventricular leads 24 and 26 also provide electrical energy to the heart 30 under certain predetermined conditions to treat various types of cardiac arrhythmia, including, for example, atrial and ventricular tachycardias, and atrial and ventricular fibrillation of the heart 30.

Figure 2:
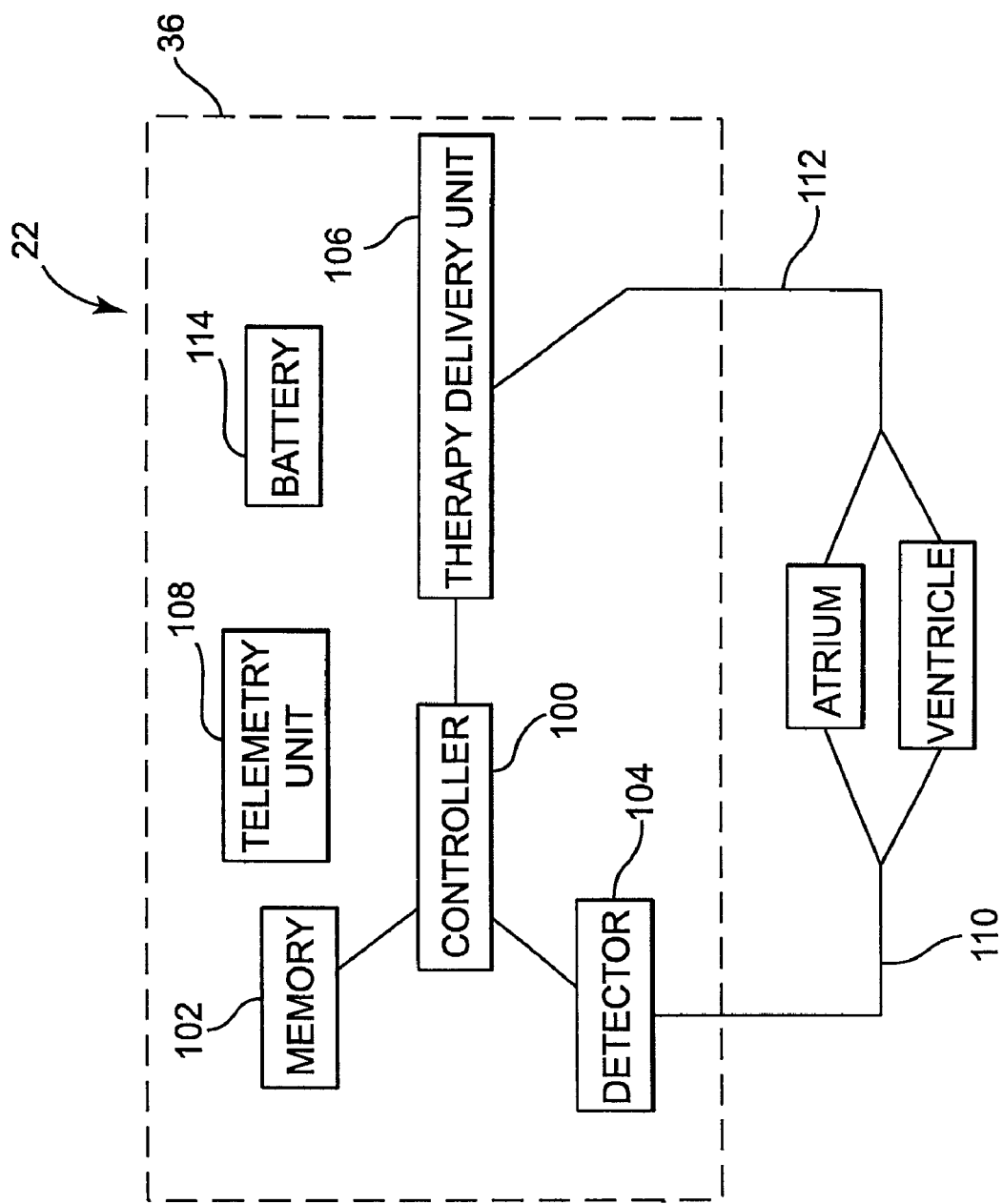
FIG. 2 is a block diagram of several components housed in the implantable medical device of FIG. 1.

A block diagram of the implantable pulse generator 22 electronics is provided in FIG. 2. The implantable pulse generator 22 includes a housing 36 which contains, among other components, a controller 100 and memory 102, which typically includes read only memory (ROM) and random access memory (RAM). Pulse generator 22 further includes a detector 104, which includes atrial and ventricular sense amplifiers (not shown), a therapy delivery unit 106, and a telemetry unit 108. The electronic components of the pulse generator 22 are interconnected by way of a bus connection (not shown).

Power to the implantable pulse generator 22 is supplied by an electrochemical battery 114 which is contained within the implantable pulse generator housing 36. The implantable pulse generator 22 is interrogated and programmed via bi-directional radio frequency telemetry through cooperative operation between the telemetry unit 108 and an external programmer in a manner known in the art.

The atrial arrhythmia detection methodologies implemented by system 20 are embodied in one or more algorithms as firmware within memory 102, and are executed by the controller 100. The detector 104 is also connected to the controller 100, and contains a plurality of electrical connections 110 coupled to the atrial and ventricular sense amplifiers. The outputs of the sense amplifiers are connected to the controller 100, such that atrial and ventricular signals received through the detector 104 are analyzed by the algorithms implemented within the controller 100. The controller 100 is also coupled to the therapy delivery unit 106, which controls the delivery of electrical energy to the heart 30 through a plurality of electrical output connections 112 to affect the sinus rhythm of the heart 30 under certain combinations of atrial 32 and ventricular 34 conditions.

Referring again to FIG. 1, a connector block 38 is mounted on the implantable pulse generator 22. The connector block 38 has two connector ports for coupling the atrial lead 24 and the ventricular lead 26 to the detector 104 and the therapy delivery unit 106 of the implantable pulse generator 22. Additional connector ports can be added to the connector block 38, as in the case of configurations having three or more ports as is known in the art. Alternatively, the connector block 38 can be provided with one connector port for coupling an implantable transvenous lead to the implantable pulse generator 22. It is understood that atrial and ventricular sensing and pacing/defibrillating functions may be accomplished using a single lead system employing atrial and ventricular conductors/electrodes, rather than by use of the dual lead system shown in FIG. 1.

It is understood that atrial and, if applicable, ventricular sensing and pacing/defibrillating functions may be accomplished using a single lead system employing atrial and, if desired, ventricular conductors/electrodes, rather than by use of the dual lead system shown in FIG. 1. In one embodiment, a single atrial lead may be used in order to accomplish the sensing and pacing/defibrillating functions associated with an atrium of the heart.

In general, the electrical activity in the heart 30 is sensed, and therapies are delivered to the heart 30, through at least one transvenous pacing/defibrillation lead connected to the implantable pulse generator 22. Unipolar and/or bipolar pacing and sensing electrodes can be used in conjunction with the transvenous pacing/defibrillation lead. In the embodiment shown in FIG. 1, bipolar leads and sensing circuits are utilized for sensing both the atrial 32 and the ventricular 34 activity. Sensing atrial activity includes the determination of atrial P-waves for purposes of determining atrial intervals. Ventricular activity is monitored by sensing for the occurrence of ventricular R-waves for purposes of determining ventricular intervals. Pacing therapies to the atrium 32 or ventricle 34 are delivered to the heart 30 using these same leads.

The system 20 may also employ defibrillation electrodes which are connected to the electrical output connections 112, and serve to deliver cardioversion and defibrillation level electrical pulses to the heart 30 as determined by the programming of controller 100. The housing 36 of the system 20 may be used as an optional defibrillation electrode, where the housing 36 of the implantable pulse generator 22 is electrically connected to a cathode pole of the therapy delivery unit 106. All defibrillation electrical pulses are delivered to the heart with at least two defibrillation electrodes, or through at least one defibrillation electrode and the housing 36 of the implantable pulse generator 22. The system 20 supports a number of pacing regimens.

In addition to the lead configuration shown in FIG. 1, the system 20 supports several other atrial lead configurations and types. For example, it is possible to use atrial endocardial bipolar pace/sensing, epicardial patches, and ancillary leads in conjunction with the implantable pulse generator 22.

In the embodiment of system 20 depicted in FIG. 1, the atrial lead 24 has an elongate body 40 having a peripheral surface 42, proximal and distal ends, 44 and 46, and a first atrial electrode 48 and a second atrial electrode 50 on the peripheral surface 42. The first atrial electrode 48 and the second atrial electrode 50 receive bipolar electrical cardiac signals from the right atrium chamber 52 of the heart 30, and are attached on the peripheral surface 42 of the elongate body 40.

The first atrial electrode 48 is situated at or adjacent to the distal end 46 of the elongate body 40 and is either a pacing tip electrode or a semi-annular or annular electrode partially or completely encircling the peripheral surface 42 of the elongate body 40. The second electrode 50 is an annular or semi-annular electrode encircling or partially encircling the peripheral surface 42 of the elongate body 40. The second electrode 50 is spaced longitudinally along the peripheral surface 42 from the first atrial electrode 48 and the distal end 46 of the atrial lead 24, such that when the atrial lead 24 is inserted into the right atrial chamber 52 of the heart 30, the first atrial electrode 48 is in physical contact with a portion of a wall of the right atrial chamber 52 of the heart 30 and the second electrode 50 is within the right atrium chamber 52.

Electrical conductors extend longitudinally within the elongate body 40 of the atrial lead 24 from a connection end at the proximal end 44 and make connection to the first and second atrial electrodes 48 and 50. The proximal end 44 of the atrial pacing lead 24 is attached to the connector block 38 of the implantable pulse generator 22. The connector block 38 provides electrical coupling between the contact ends of the electrical conductors of atrial lead 24 with the atrial sense amplifier of the detector 104 and the therapy delivery unit 106, such that the implantable pulse generator 22 receives bipolar signals from and delivers bipolar pacing to the right atrium 52 of the heart 30.

The ventricular lead 26, if used in combination with the atrial lead 24, includes an elongate body 54 having a peripheral surface 56, proximal and distal ends, 58 and 60, and a ventricle pacing electrode 62. The ventricular lead 26 also includes a first defibrillation electrode 64 and a second defibrillation electrode 66 situated on the peripheral surface 56 of the elongate body 54. The ventricular pacing electrode 62 and the first defibrillation electrode 64 are adapted to receive electrical cardiac signals from the right ventricle chamber 68 of the heart 30, and are attached on the peripheral surface of the elongate body 54. The second defibrillation electrode 66 is spaced apart and longitudinally on the peripheral surface 56 of the ventricular lead 26. This configuration affords positioning of the ventricular lead 26 in the heart 30 with the ventricular pacing electrode 62 in the apex of the right ventricle 68, the first defibrillation electrode 64 within the right ventricle chamber of the heart, and the second defibrillation electrode 66 within the right atrium chamber 52 or a major vein leading to the right atrium.

Electrical leads extend longitudinally within the elongate body 54 of the ventricular lead 26 from a connection end at the proximal end 58 to make connection with the ventricular pacing electrode 62, the first defibrillation electrode 64, and the second defibrillation electrode 66. The proximal end 58 of the ventricular lead 26 is attached to the connector block 38 of the implantable pulse generator 22. The connector block 38 provides for electrical coupling between the contact ends of the electrical conductors of ventricular lead 26 with the ventricular sense amplifier of the detector 104 and the therapy delivery unit 106, such that the implantable pulse generator 22 receives either unipolar or bipolar signals from, and can deliver unipolar or bipolar pacing to, the right ventricle 68 and defibrillation electrical pulses to the ventricles 34 of the heart 30.

The atrial lead 24 and, if applicable, the ventricular lead 26 are releasably attached to, and are separated from, the implantable pulse generator 22 to facilitate insertion of the leads 24, 26 into the heart 30. The proximal end 44 of the atrial lead 24 and the proximal end 58 of the ventricular lead 26 are adapted to seal together with the connector ports of the implantable pulse generator 22 to thereby engage the contact ends of the atrial lead 24 and the ventricular lead 26 with the plurality of electrical connections 110 and the therapy delivery unit 106 of the implantable pulse generator 22. The implantable pulse generator 22 of the system 20 is then positioned subcutaneously within the body 28.

Figure 3:
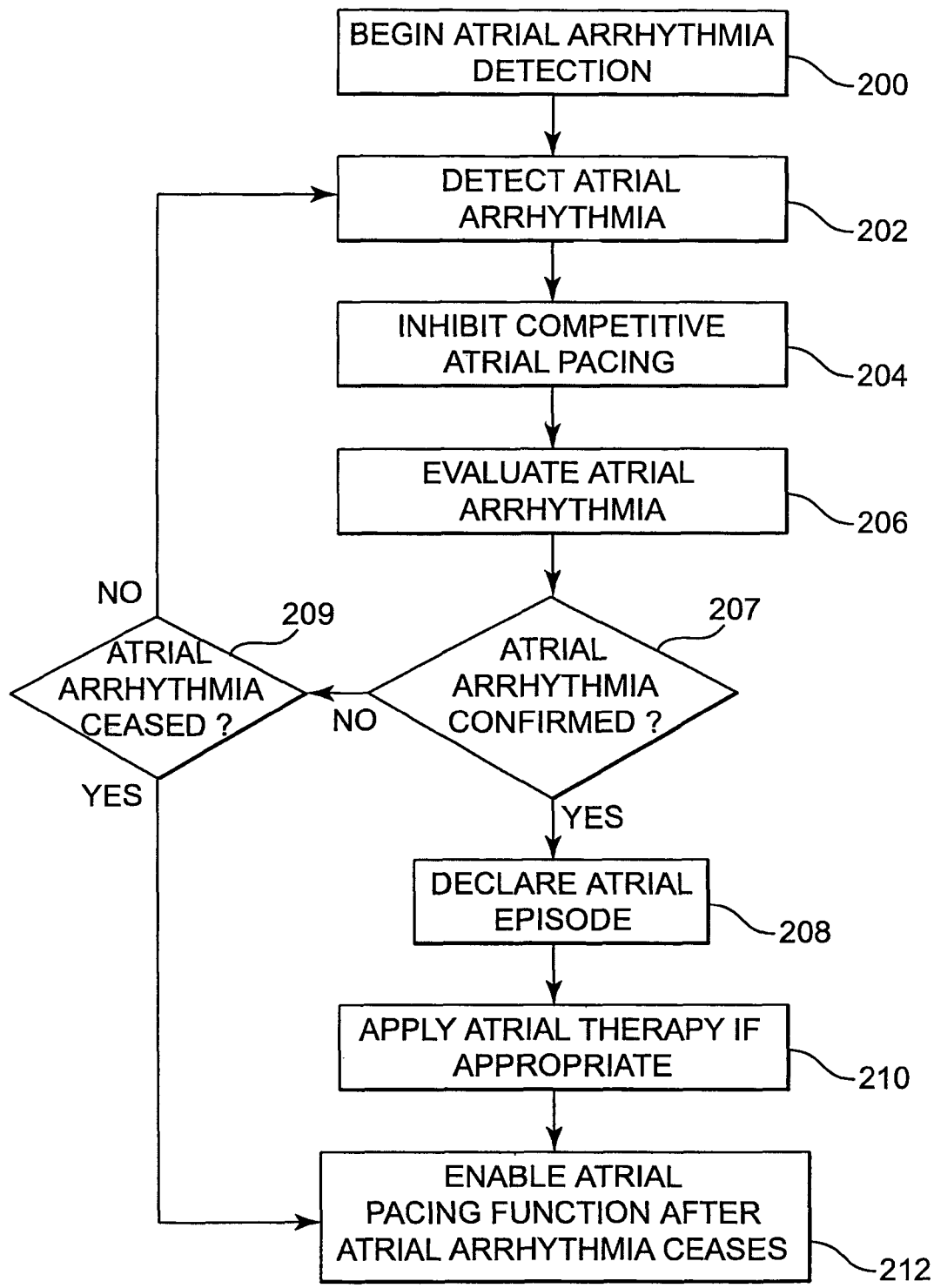
FIG. 3 is a flow chart depicting various processes of an atrial arrhythmia detection methodology in accordance with an embodiment of the present invention.

Referring now to FIG. 3, there is shown a flow diagram that describes various processes involving an atrial arrhythmic detection methodology in accordance with an embodiment of the present invention. The methodology depicted in FIG. 3 may be implemented using IMD circuitry described hereinabove.

Atrial arrhythmias are, in general terms, dysrhythmias of the atria, which may include a variety of atrial tachycardias, including atrial fibrillation, atrial flutter, inappropriate sinus tachycardia, and paroxysmal supraventricular tachycardias, for example. Because many of these atrial arrhythmias have potential long term consequences, such as tachycardia-mediated cardiomyopathy, as well as the development of chronic atrial fibrillation from other atrial tachyarrhythmias, appropriate detection and treatment is important.

It has been found by the inventors that conventional treatment therapies that involve atrial pacing to regulate atrial activity in response to certain atrial arrhythmias may have the unintended effect of slowing the atrial arrhythmia detection and confirmation process. In particular, it has been determined by the inventors that delivery of atrial pacing during the atrial arrhythmia detection and confirmation process results in a reduction in the rate at which atrial arrhythmia detection can be accomplished. An A-A interval that ends with an atrial pace is considered a "slow" atrial interval. Application of an atrial arrhythmia detection scheme that processes such "slow" atrial intervals disadvantageously arrives at a detection decision at a reduced speed.

An atrial arrhythmia detection methodology of the present invention advantageously avoids processing of slow atrial intervals and, as a result, arrives at a detection decision at an increased speed relative to conventional detection techniques. An atrial arrhythmia detection methodology of the present invention provides for increased atrial arrhythmia detection and confirmation by inhibiting atrial pacing during a time in which the atrial arrhythmias are evaluated. Inhibiting atrial pacing during such period of evaluation advantageously prevents the occurrence of slow atrial intervals.

Figure 6:
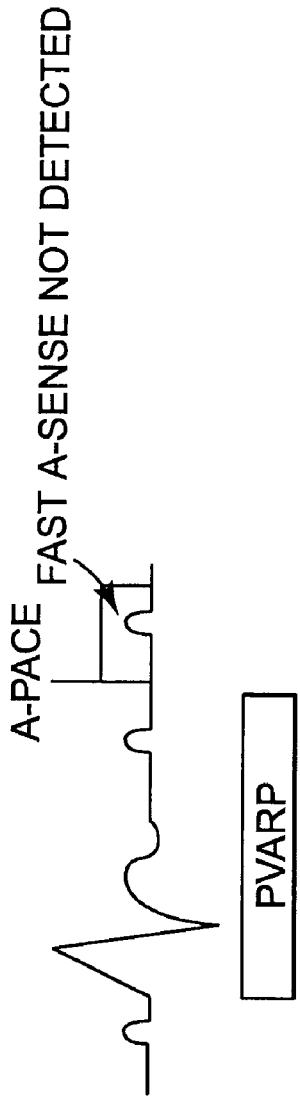
FIG. 6 illustrates the delivery of an atrial pace during a detected atrial arrhythmia which disadvantageously reduces the rate of atrial detection decisions.
Figure 7:
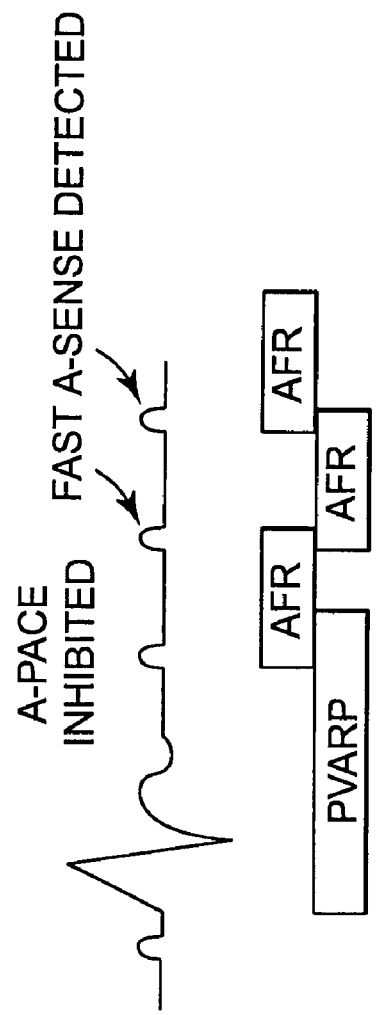
FIG. 7 illustrates inhibiting of an atrial pace during a detected atrial arrhythmia which advantageously increases the rate of atrial detection decisions according to an embodiment of the present invention.

FIGS. 6 and 7 respectively illustrate the effects of providing for (FIG. 6), and inhibiting (FIG. 7), atrial paces during a detected atrial arrhythmia. FIG. 6 illustrates the delivery of an atrial pace during a detected atrial arrhythmia which disadvantageously reduces the rate of atrial detection decisions. FIG. 7 illustrates inhibiting of an atrial pace during a detected atrial arrhythmia which advantageously increases the rate of atrial detection decisions according to an embodiment of the present invention.

With regard to FIG. 6, the fast atrial sense following the atrial pace is not detected, thereby precluding this fast atrial sense from being captured and evaluated in an atrial window. It can be appreciated that excluding this and other fast atrial sense samples following atrial paces as shown in FIG. 6 reduces the rate at which atrial detection window decisions can be accomplished.

In accordance with the principles of the present invention, atrial paces are inhibited during a transitional period in which atrial activity is detected as progressing from a normal condition to an arrhythmic condition. This transitional period may also be characterized as a period in which ventricular rhythm management is disassociated from atrial activity (i.e., atrial tracking) as a result of detecting rapid fast atrial responses. Delivery of pacing signals to the atrium is inhibited upon detecting atrial arrhythmia during this transitional period. Inhibiting atrial paces during this transitional period advantageously increases the rate at which a detected atrial arrhythmia is confirmed.

According to one embodiment, an atrial flutter response (AFR) mechanism of system 20 is provided to prevent pacing into the atrial vulnerable period and to provide immediate fallback for atrial rates higher than an AFR programmable rate. This fallback is maintained as long as atrial events continually exceed the AFR programmable rate. The term fallback is generally understood in the art as a programmed rate, in the context of dual-chamber pacing/defibrillation devices, to which the ventricular pacing rate falls back when the upper atrial rate limit has been exceeded due to atrial tachyarrhythmia. It is to be understood that the AFR mechanism described herein is applicable to any type of atrial arrhythmia, and that the AFR nomenclature is used for convenience only.

When, for example, AFR provided by the system 20 is programmed to 170 bpm, a detected atrial event inside the PVARP or a previously triggered AFR interval will start an AFR window of a given duration (e.g., 350 ms). It is understood that the programmable AFR window duration may be varied, such as between 260 ms and 460 ms, for example. FIG. 7 shows a first AFR window initiated in response to a detected atrial event toward the end of the PVARP. Atrial detection inside the AFR window is classified as refractory sensed and is not tracked. Tracking starts only after both the AFR and the PVARP durations have expired.

Paced atrial events scheduled inside an AFR window are delayed (i.e., inhibited) until the AFR window has expired, as is shown in FIG. 7. According to one approach, if there are fewer than 50 ms remaining before a ventricular pace, the atrial pace is inhibited for the cycle. The ventricular pace is not affected by AFR and will take place as scheduled. High-rate atrial sensing may continuously re-trigger the AFR window (i.e., extend the AFR window), effectively resulting in fallback to an appropriate pacing mode (e.g., VDI(R)). FIG. 7 illustrates two subsequent AFR windows initiated after the first AFR window due to this re-triggering mechanism. Inhibiting atrial paces during atrial flutter or other high rate atrial activity advantageously provides for fast atrial sensing to be detected, thereby providing for faster satisfaction of atrial detection windows and, ultimately, faster detection decisions.

It has also been found that if the atrium is paced too soon after an atrial sense depolarization signal is sensed, it is theoretically possible that such premature delivery of an atrial pace signal can induce an atrial arrhythmia. Inhibiting an atrial pacing function in this case prevents induced atrial arrhythmias of this nature from occurring.

In accordance with one embodiment of the present invention, and with particular reference to FIG. 3, the system 20 initiates atrial arrhythmia detection 200, such detection typically being an ongoing function of the system 20. The system 20 is programmed to implement several types of atrial arrhythmia detection algorithms as are known in the art to detect 202 atrial arrhythmia, such as atrial flutter for example. In response to detecting atrial arrhythmia, the system 20 inhibits 204 atrial pacing to prevent competitive atrial pacing during a period of further evaluation.

The atrial arrhythmia is evaluated 206 while atrial pacing is inhibited according to the detection algorithm employed by the system 20. If an atrial arrhythmia condition is confirmed 207 by the system 20, an atrial episode is declared 208. Atrial therapy may be applied 210, if appropriate, upon declaring the presence of a confirmed atrial episode. The capability to deliver atrial pacing signals to the atrium is enabled 212 at an appropriate time, typically after the atrial arrhythmia (e.g., atrial flutter) has ceased.

If an atrial arrhythmia condition is not confirmed 207 and the atrial arrhythmia has not ceased 209, the detection, inhibiting, and evaluation processes 202, 204, 206 are repeated. If an atrial arrhythmia condition is not confirmed 207 and the atrial arrhythmia has ceased 209, the capability to deliver atrial pacing signals to the atrium is enabled 212.

Figure 4:
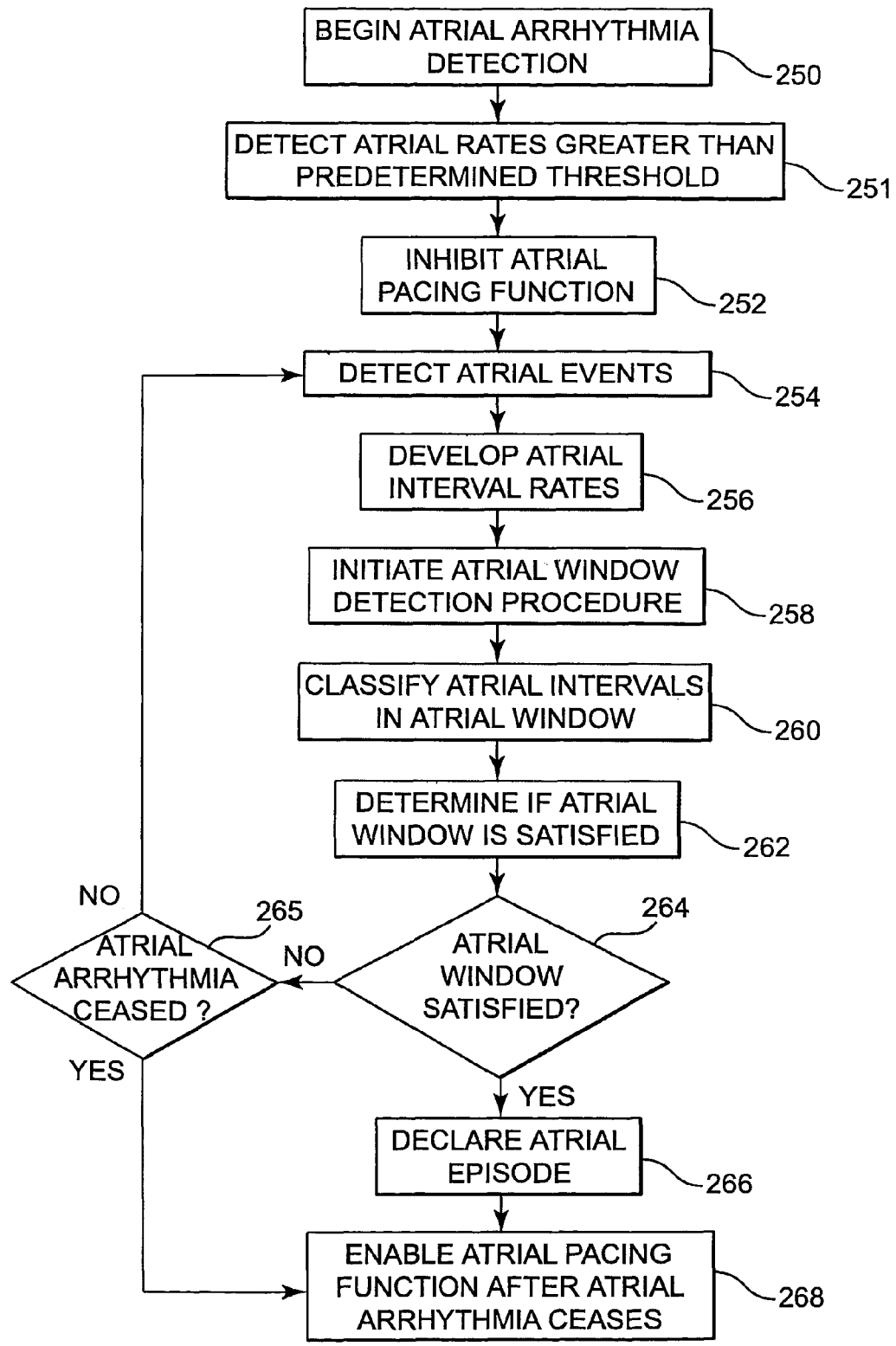
FIG. 4 is a flow chart depicting various processes of an atrial arrhythmia detection methodology in accordance with another embodiment of the present invention.

FIG. 4 depicts various processes involving an atrial arrhythmia detection methodology according to another embodiment of the present invention. According to this embodiment, and upon implementing 250 the atrial arrhythmia detection algorithm, atrial interval rates are detected 251 and compared to a predetermined rate threshold. For example, the predetermined rate threshold may be indicative of an atrial rate associated with atrial flutter (e.g., 230 bpm). If the detected atrial rate exceeds the predetermined rate threshold, atrial pacing is inhibited 252 so as to avoid competitive atrial pacing.

The system 20 detects the occurrence of atrial events 254, from which atrial interval rates are developed 256 in a manner known in the art. Detecting atrial events 254 typically involves sensing of atrial P-waves. An atrial interval rate (i.e., an A-A wave time interval) is computed using the detected atrial P-waves. An average atrial interval rate may also be computed.

An arrhythmia detection methodology of the present invention preferably employs a detection window when analyzing atrial rhythms. Upon initiation 258 of an atrial detection window procedure, an atrial detection window is employed to classify 260 atrial intervals. The detection parameters of the atrial window, such as window length and satisfaction criteria, may be selected to provide for enhanced detection and response to atrial arrhythmia episodes.

Each detected atrial interval rate processed in the atrial window is compared to an atrial rate threshold as part of the atrial interval classification process 260. Based on this comparison, the atrial interval rate is classified relative to one or more thresholds, such as rate thresholds. A detected atrial rate is classified as being a fast atrial interval, for example, if the atrial interval rate exceeds a given atrial rate threshold. The atrial interval rate may also be classified as slow based on another threshold.

The atrial interval rate samples buffered in the atrial window are evaluated to determine 262 if and when the atrial window is satisfied. The atrial window is satisfied when a predetermined number of the most current atrial intervals meet a preestablished satisfaction criterion. For example, the satisfaction criterion associated with the atrial window may be defined as n of the last m atrial intervals being classified as fast atrial intervals. The satisfaction criterion may, for example, be expressed as a number (i.e., an integer), percentage or ratio.

Once the atrial window becomes satisfied 264, and typically after performing one or more additional verification processes, an atrial episode is declared 266. Atrial pacing is subsequently enabled 268 (i.e., not withheld or inhibited) after the detected atrial arrhythmia has ceased. If the atrial detection window is not satisfied 264 and the atrial arrhythmia has not ceased 265, the system 20 returns to the atrial detection process 254. If the atrial detection window is not satisfied 264 and the atrial arrhythmia has ceased 265, the capability to deliver atrial pacing signals to the atrium is enabled 268.

As was discussed above, an A-A interval that ends with an atrial pace is defined as a slow interval. If the atrial pacing function is not inhibited during atrial arrhythmia evaluation, atrial paces will likely be interspersed with fast atrial senses. By inhibiting the atrial pacing function, the criteria for satisfying the atrial detection window occurs sooner as compared to detection techniques that allow for atrial pacing during atrial arrhythmia detection. Satisfying the atrial detection window sooner provides for a more expeditious initiation of atrial therapy delivery, when appropriate.

Figure 5A:
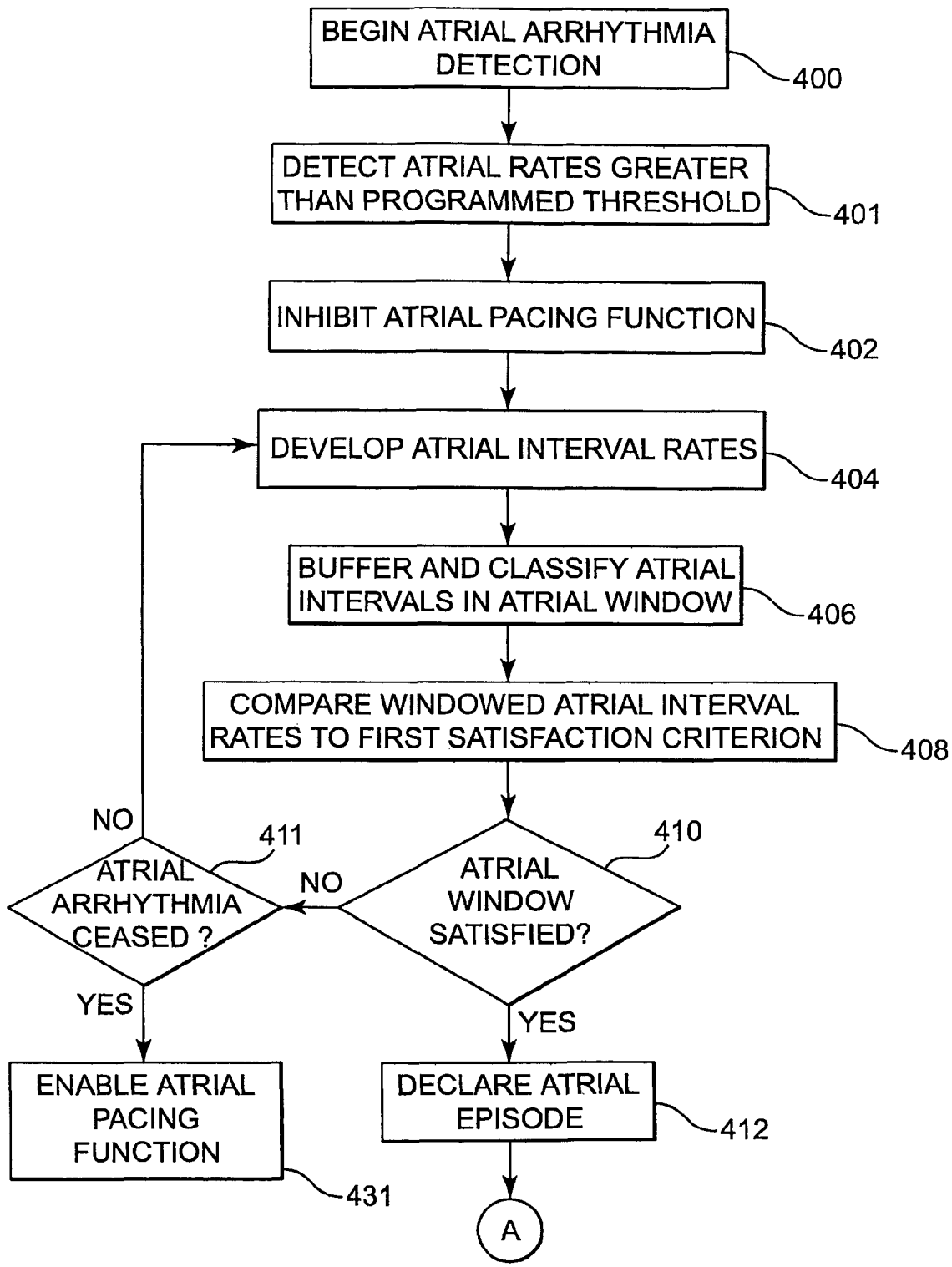
FIGS. 5A-5B are flow charts depicting various processes of an atrial arrhythmia detection methodology in accordance with yet another embodiment of the present invention.

FIG. 5 illustrates several operations associated with an atrial arrhythmia detection methodology according to another embodiment of the present invention. It is understood that the detection and classification operations depicted in FIG. 5 may be performed in connection with a multiple rate zones implementation, but that a single rate zone is assumed in the description of FIG. 5 for purposes of clarity of explanation. Moreover, duration timers may be employed in the embodiment of FIG. 5, but are not included in the discussion of this embodiment for purposes of clarity of explanation.

After initiating the atrial arrhythmia detection process 400, atrial interval rates are detected 401 and compared to a predetermined rate threshold. If the detected atrial rate exceeds the predetermined rate threshold, atrial pacing is inhibited 402 under conditions discussed previously. Atrial events are detected, from which atrial intervals are developed 404. Atrial interval rates are buffered and classified 406 in an atrial detection window of length L=X, where X typically ranges between 20 and 60 atrial interval rate samples.

The windowed atrial interval rates are compared 408 to a first satisfaction criterion. According to one configuration, for example, the first satisfaction criterion associated with the atrial window is defined as 32 of the last 40 atrial intervals (80%) classified as fast atrial intervals. The comparison is made to determine if the atrial window is satisfied 410. If the atrial detection window is not satisfied 410 and the atrial arrhythmia has not ceased 411, the system 20 returns to the atrial detection process 404. If the atrial detection window is not satisfied 410 and the atrial arrhythmia has ceased 411, the capability to deliver atrial pacing signals to the atrium is enabled 431.

Figure 5B:
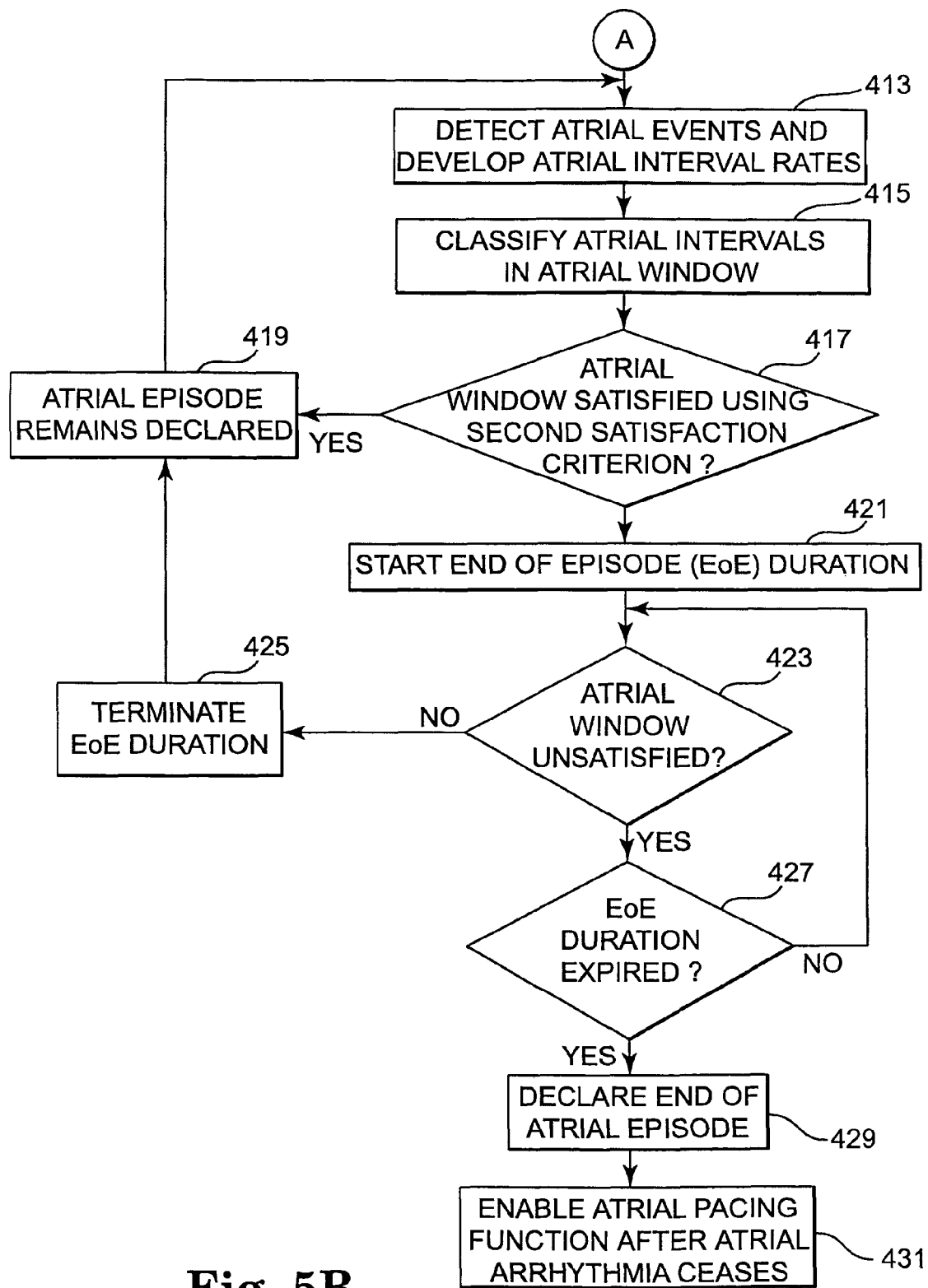

FIG. 5B illustrates various processes associated with ending an atrial episode. According to the embodiment shown in FIG. 5B, and after an atrial episode has been declared 412, atrial events are detected from which atrial interval rates are developed 413. Atrial intervals are classified 415 in the atrial window. If the atrial window remains satisfied 417, as measured against a maintenance satisfaction criterion (e.g., 24 of the last 40 (60%) atrial intervals classified as fast), the system 20 considers the same atrial episode to remain declared 419. The detection and classification processes 413, 415, 417 are repeated.

If the atrial window becomes unsatisfied 417, such that the maintenance satisfaction criterion is not met, an End of Episode (EoE) duration is initiated 421. If the atrial window becomes satisfied 423 during the EoE duration, the EoE duration is terminated 425, and the system 20 considers the same atrial episode to remain declared 419. The detection and classification processes 413, 415, 417 are repeated.

If the atrial window remains unsatisfied 423 during and at the expiration 427 of the EoE duration, the system 20 declares 429 the atrial episode to have ended. The system 20 returns to the detection, classification, and windowing processes depicted in FIG. 5A.

All or portions of an atrial arrhythmia detection methodology according to the present invention may be incorporated as part of new or existing arrhythmia detection schemes. For example, an exemplary dual atrial and ventricular windowing methodology for detecting and verifying atrial and ventricular arrhythmias is disclosed in U.S. Pat. No. 6,658,286 entitled "Atrial and Ventricular Tachyarrhythmia Detection System and Method," which is hereby incorporated herein by reference. The atrial pacing inhibiting methodologies of the present invention may also be implemented in the context of the atrial and ventricular detection approaches disclosed in commonly owned U.S. Pat. No. 5,978,707, which is hereby incorporated herein by reference. These or other known atrial or combined atrial/ventricular arrhythmia detection methodologies may be employed in combination with the present invention.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method implemented with an implantable medical device capable of sensing and pacing at least an atrium of a heart, comprising:
   detecting, during an atrial arrhythmia, atrial events occurring within a post-ventricular atrial refractory period (PVARP);
   initiating a detection window in response to the detected atrial events, the detection window having a length and a satisfaction criterion;
   inhibiting delivery of atrial pace signals for a duration of the detection window;
   classifying, while inhibiting delivery of atrial pace signals, atrial intervals in the detection window; and
   declaring an atrial episode in response to satisfying the detection window by evaluating the atrial intervals in the detection window with respect to the satisfaction criterion.

2. The method of claim 1, wherein inhibiting delivery of the atrial pace signals comprises inhibiting delivery of the atrial pace signals in response to detecting atrial interval rates indicative of atrial flutter.

3. The method of claim 1, wherein inhibiting delivery of the atrial pace signals comprises inhibiting delivery of the atrial pace signals in response to detecting atrial interval rates of at least about 130 bpm.

4. The method of claim 1, wherein inhibiting delivery of the atrial pace signals comprises inhibiting delivery of the atrial pace signals to cause an increase in a rate of detection window satisfaction.

5. The method of claim 1, further comprising enabling delivery of the atrial pace signals to the atrium after ceasing of the atrial arrhythmia.

6. The method of claim 1, wherein the detection window length ranges between 20 and 60 atrial interval samples.

7. The method of claim 1, wherein the satisfaction criterion represents a predetermined number, percentage or ratio of the atrial intervals classified as fast atrial intervals relative to the detection window length.

8. The method of claim 1, wherein the satisfaction criterion represents about 80 percent of the atrial intervals classified as fast atrial intervals.

9. The method of claim 1, further comprising verifying that the declared atrial episode is a sustained atrial episode in response to the detection window being satisfied by a second satisfaction criterion for subsequent atrial intervals.

10. The method of claim 9, wherein each of the satisfaction criterion and second satisfaction criterion represents a predetermined number, percentage or ratio of the atrial intervals classified as fast atrial intervals relative to the detection window length, and the second satisfaction criterion is less than the satisfaction criterion.

11. The method of claim 10, wherein the satisfaction criterion represents about 80 percent of the atrial intervals classified as fast atrial intervals and the second satisfaction criterion represents about 60 percent of the subsequent atrial intervals classified as fast atrial intervals.

12. A body implantable system, comprising:
   at least one lead comprising an atrial electrode for sensing and pacing an atrium of a heart;
   energy delivery circuitry coupled to the at least one lead;
   a detector, coupled to the at least one lead, configured to detect atrial events occurring within a post-ventricular atrial refractory period (PVARP) during an atrial arrhythmia;
   memory configured to define a detection window having a length and a satisfaction criterion; and
   a control circuit coupled to the energy delivery circuitry, detector and memory, the control circuit configured to initiate the detection window in response to the detected atrial events, inhibit delivery of atrial pace signals for a duration of the detection window, classify, while inhibiting delivery of atrial pace signals, atrial intervals in the detection window, and declare an atrial episode in response to satisfying the detection window by evaluating the atrial intervals in the detection window with respect to the satisfaction criterion.

13. The system of claim 12, wherein the control circuit is configured to inhibit delivery of the atrial pace signals in response to detecting atrial interval rates indicative of atrial flutter.

14. The system of claim 12, wherein the control circuit is configured to inhibit delivery of the atrial pace signals in response to detecting atrial interval rates of at least about 130 bpm.

15. The system of claim 12, wherein the control circuit is configured to inhibit delivery of the atrial pace signals to cause an increase in a rate of detection window satisfaction.

16. The system of claim 12, wherein the control circuit is configured to enable delivery of the atrial pace signals to the atrium after cessation of the atrial arrhythmia.

17. The system of claim 12, wherein the detection window length ranges between 20 and 60 atrial interval samples.

18. The system of claim 12, wherein the satisfaction criterion represents a predetermined number, percentage or ratio of the atrial intervals classified as fast atrial intervals relative to the detection window length.

19. The system of claim 12, wherein the satisfaction criterion represents about 80 percent of the atrial intervals classified as fast atrial intervals.

20. The system of claim 12, wherein the control circuit is configured to verify that the declared atrial episode is a sustained atrial episode in response to the detection window being satisfied by a second satisfaction criterion for subsequent atrial intervals.

21. The system of claim 20, wherein each of the satisfaction criterion and second satisfaction criterion represents a predetermined number, percentage or ratio of the atrial intervals classified as fast atrial intervals relative to the detection window length, and the second satisfaction criterion is less than the satisfaction criterion.

22. The system of claim 21, wherein the satisfaction criterion represents about 80 percent of the atrial intervals classified as fast atrial intervals and the second satisfaction criterion represents about 60 percent of the subsequent atrial intervals classified as fast atrial intervals.

23. A body implantable system, comprising:
 means for detecting atrial events occurring within a post-ventricular atrial refractory period (PVARP) during an atrial arrhythmia;
 means for initiating a detection window in response to the detected atrial events, the detection window having a length and a satisfaction criterion;
 means for inhibiting delivery of atrial pace signals for a duration of the detection window;
 means for classifying, while inhibiting delivery of atrial pace signals, atrial intervals in the detection window; and
 means for declaring an atrial episode in response to satisfying the detection window by evaluating the atrial intervals in the detection window with respect to the satisfaction criterion.

24. The system of claim 23, comprising means for enabling delivery of the atrial pace signals to the atrium after cessation of the atrial arrhythmia.

25. The system of claim 23, comprising means for verifying that the declared atrial episode is a sustained atrial episode in response to the detection window being satisfied by a second satisfaction criterion for subsequent atrial intervals.

\* \* \* \* \*